US005606087A

United States Patent [19]

Roberg et al.

[11] Patent Number: 5,606,087
[45] Date of Patent: Feb. 25, 1997

[54] PROCESS FOR MAKING ALUMINOXANES

[75] Inventors: John K. Roberg; Robert E. Farritor; Edward A. Burt, all of Baton Rouge, La.

[73] Assignee: Albemarle Corporation, Richmond, Va.

[21] Appl. No.: 635,358

[22] Filed: Apr. 19, 1996

[51] Int. Cl.$^6$ .................................................. C07F 5/06
[52] U.S. Cl. ...................................... 556/179; 423/625
[58] Field of Search ........................... 556/179; 423/625

[56] References Cited

U.S. PATENT DOCUMENTS

| | | | |
|---|---|---|---|
| 3,219,591 | 11/1965 | Vandenberg | 252/431 |
| 3,242,099 | 3/1966 | Manyik | 252/429 |
| 3,300,458 | 1/1967 | Manyik | 260/88.2 |
| 4,730,071 | 3/1988 | Schoenthal et al. | 556/179 |
| 4,730,072 | 3/1988 | Schoenthal et al. | 556/179 |
| 4,772,736 | 9/1988 | Edwards et al. | 556/179 |
| 4,908,463 | 3/1990 | Bottelberghe | 556/179 |
| 4,924,018 | 5/1990 | Bottelberghe | 556/179 |
| 4,937,363 | 6/1990 | Smith, Jr. et al. | 556/179 |
| 4,960,878 | 10/1990 | Crapo et al. | 556/179 |
| 4,968,827 | 11/1990 | Davis | 556/179 |
| 5,041,584 | 8/1991 | Crapo et al. | 556/179 |
| 5,041,585 | 8/1991 | Deavenport et al. | 556/179 |
| 5,086,024 | 2/1992 | Crapo et al. | 502/117 |
| 5,206,401 | 4/1993 | Deavenport et al. | 556/175 |
| 5,403,942 | 4/1995 | Becker et al. | 556/175 |
| 5,427,992 | 6/1995 | Graefe et al. | 502/111 |

OTHER PUBLICATIONS

Manyik et al., A Soluble Chromium–Based Catalyst for Ethylene Trimerization and Polymerization, Journal of Catalysis, vol. 47, 1977, pp. 197–209.

Primary Examiner—Paul F. Shaver
Attorney, Agent, or Firm—Philip M. Pippenger

[57] ABSTRACT

An improved process for making aluminoxanes by the addition of water to a solvent solution of a hydrocarbylaluminum compound and/or an aluminoxane feeds the water through an orifice which is surrounded by a flow of solvent which carries the water into the solvent solution of hydrocarbylaluminum compound and/or aluminoxane.

6 Claims, 3 Drawing Sheets

PROCESS FOR MAKING ALUMINOXANES

This invention relates generally to the making of aluminoxanes and more specifically to an improved process for making aluminoxanes by the addition of free water to hydrocarbylaluminum compounds such as trimethylaluminum.

Vandenberg, U.S. Pat. No. 3,219,591 reported the catalytic activity of compounds formed by the reaction of trialkylaluminum with limited amounts of water in the polymerization of epichlorohydrin and other oxiranes. Shortly thereafter, Manyik, et al. U.S. Pat. No. 3,242,099 reported the use of aluminoxanes, made by reacting 0.85–1.05 moles of water with hydrocarbylaluminum compounds such as triisobutylaluminum, as co-catalysts with certain transition metal compounds in the polymerization of mono-unsaturated alphaolefins; e.g. ethylene and propylene. Isobutylaluminoxane was also made by adding an equal mole quantity of water to a heptane solution of triisobutylaluminum.

Manyik, et al. U.S. Pat. No. 3,300,458 prepare alkylaluminoxane by passing a hydrocarbon through water to form a wet hydrocarbon and mixing the wet hydrocarbon and an alkyl aluminum/hydrocarbon solution in a conduit.

Schoenthal, et al. U.S. Pat. No. 4,730,071 show the preparation of methylaluminoxane by dispersing water in toluene using an ultrasonic bath to cause the dispersion and then adding a toluene solution of trimethylaluminum to the dispersion. Schoenthal, et al. U.S. Pat. No. 4,730,072 is similar except it uses a high speed, high shear-inducing impeller to form the water dispersion.

Edwards, et al. U.S. Pat. No. 4,772,736 describe an aluminoxane preparation process in which water is introduced below the surface of a solution of hydrocarbylaluminum adjacent to a stirrer which serves to immediately disperse the water in the hydrocarbon solution.

Bottelberghe U.S. Pat. No. 4,908,463 describe an aluminoxane preparation process in which a static mixer is used to disperse water in a solvents and then impinges the water dispersion with a hydrocarbylaluminum solution in a T-shaped reactor. The solution is then removed to a finished reaction vessel which is stirred and can have a cooling means such as a heat-exchanger in an external pump-around loop.

Becker et al U.S. Pat. No. 5,403,942 and Graefe et al. U.S. Pat. No. 5,427,992 describe batch processes for preparing aluminoxanes by injecting water into trialkylaluminum solutions using respectively, a jet loop reactor and a rotor/stator machine to mix the water and trialkylaluminum.

A problem associated with the direct addition of free water to solvent solution of hydrocarbylaluminum in order to form aluminoxanes is plugging of the orifice of the water delivery system. This is caused by local over oxidation of the hydrocarbyl aluminum to form insoluble products and can occur even when using a solution or dispersion of water in solvent. The plugging problem requires the orifice to be periodically cleaned which interrupts the aluminoxane production process. We have now found a method for reducing or eliminating the plugging problem.

In accordance with this invention there is provided an improved process for making aluminoxane compositions by the addition of water to a solvent solution of a hydrocarbylaluminum and/or an aluminoxane, the improvement comprising feeding said water through an orifice which is surrounded by a flow of solvent which carries said water into said solvent solution.

Figure 1:
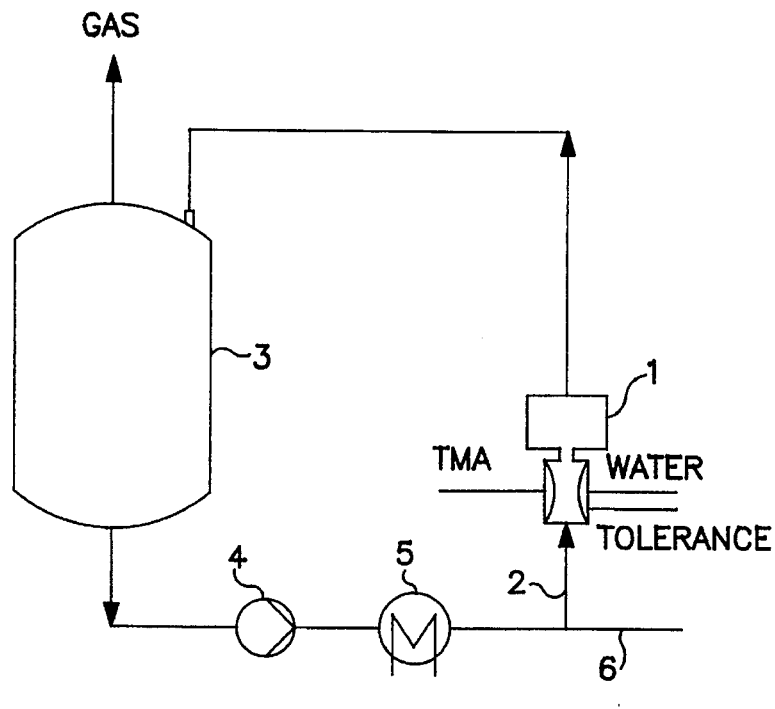
FIG. 1 is a schematic diagram showing a pumparound reactor system used in the embodiment of the process of the invention described in Example 1.

Hydrocarbylaluminoxanes may exist in the form of linear, cyclic, caged or polymeric structures with the simplest compounds being a tetraalkylaluminoxane such as tetramethylaluminoxane, $(CH_3)_2AlOAl(CH_3)_2$, or tetraethylaluminoxane, $(C_2H_5)_2AlOAl(C_2H_5)_2$. The compounds preferred for use in olefin polymerization catalysts are oligomers, sometimes referred to as polyethylaluminoxanes, and usually contain about 4 to 20 of the repeating units:

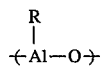

where R is $C_1$–$C_8$ alkyl and is preferably methyl. The exact structure of aluminoxanes has not been defined and they may contain linear, cyclic, caged and/or cross-linked species. Methylaluminoxanes (MAOs) normally have lower solubility in organic solvents than higher alkylaluminoxanes and the methylaluminoxane solutions tend to be cloudy or gelatinous due to the separation of particles and agglomerates. In order to improve the solubility of the methylaluminoxane, higher alkyl groups, e.g. $C_2$ to $C_{20}$ can be included such as by hydrolyzing a mixture of trimethylaluminum with up to 50 mole percent of a $C_2$ to $C_{20}$ alkylaluminum compound such as, for example, triethylaluminum, tri-n-propylaluminum, triisobutylaluminum, tri-n-hexylaluminum, tri-n-octylaluminum or a triarylaluminum. The MAO's can also contain up to about 20 mole percent, based on aluminum, of moieties derived from amines, alcohols, ethers, esters, phosphoric and carboxylic acids, thiols, alkyl and aryl disiloxanes and the like to further improve activity, solubility and/or stability. Such modified and mixed methylhigher alkyl or aryl aluminoxanes are included in the term "methylaluminoxane" as used herein.

Any hydrocarbyl aluminum compound or mixture of compounds capable of reacting with water to form an aluminoxane can be used. This includes, for example, trialkylaluminum, triarylaluminum, mixed alkyl arylaluminum, alkylaluminum hydride and the like.

The preferred hydrocarbyl aluminum compounds are the alkylaluminum compounds, especially trialkylaluminum compounds such as trimethylaluminum, triethylaluminum, triisobutylaluminum, tri-n-hexylaluminum, trioctylaluminum and the like. Of these, the more preferred are the tri-$C_{1-4}$-alkylaluminum compounds.

The process of the invention also includes the addition of water to preformed aluminoxanes and/or mixtures of aluminoxanes and hydrocarbyl aluminum compounds so as to form modified aluminoxane compositions by the further reaction of such materials with water.

The reaction is carried out in an inert solvent. Any inert solvent can be used. The preferred solvents are aliphatic and aromatic hydrocarbons. Aromatic hydrocarbons are more preferred such as toluene, xylene, ethylbenzene, cumene, mesitylene and the like. The most preferred solvent is toluene.

The water can be added to the reaction either neat and/or dissolved or dispersed in the solvent. The reactants are combined in proportions to provide from about 0.5 to 8.0 moles of hydrocarbyl aluminum compound per mole of water. When making methylaluminoxanes, the proportions are preferably from about 1.3 to 6.0 moles of trimethylaluminum and more preferably from about 2.0 to 4.0 moles per mole of water.

The reaction temperature ranges from about −70° to 100° C. with a preferred range of about −50° to 50° C. and a more preferred range of from about −20° to 20° C.

Figure 3:
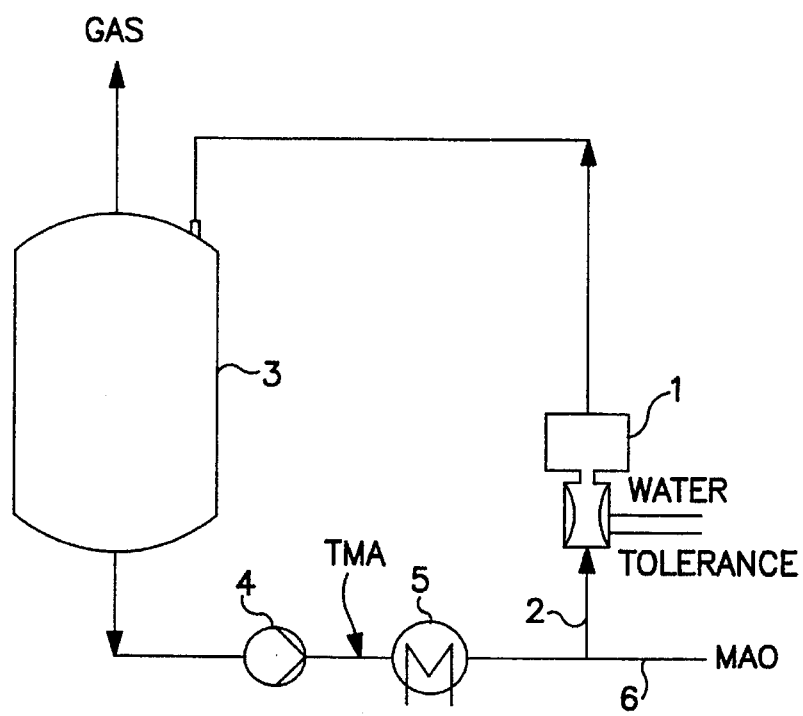
FIG. 3 is a schematic diagram showing a pumparound reactor system used in the embodiment of the process of the invention described in Examples 2 and 3.

In the embodiment of the process of the invention which is illustrated in FIG. 1, water, trimethylaluminum (TMA) and toluene are continuously injected into the inlet of an inline mixer 1 which is located in a reactor loop 2. Alternatively TMA can be fed to the reactor at a different point, for example, between pump 4 and cooler 5 as illustrated in FIG. 3. The water and TMA react and the reaction mixture, which includes product methylaluminum (MAO) and unreacted TMA, are circulated through loop 2 to degassing tank 3 where methane gas is vented. The reaction mixture is then pumped back to the inlet of in-line mixer 1 such as an IKA Works in-line disperser, whose rotor operates at speeds of from about 7,000 to 13,000 rpm, by pump 4. The heat of reaction is maintained within a selected temperature range by use of cooler 5. MAO product in solvent, which contains unreacted TMA, is continuously drawn off through line 6. TMA and solvent can be flashed from the crude MAO product and returned, for example, to degasser 3 or to line 2 ahead of the in-line mixer. The in-line mixer produces a homogeneous reaction zone and the large volume recycle of product stream provides both heat absorption and dilution of the reactants, especially the water, such that localized overheating and/or any significant temperature rise is avoided. The continuous introduction of reactant and withdrawal of product permits a constant concentration of reactants to be maintained in a steady state reaction which helps to achieve a more uniform and reproducible product in improved yields. It also permits the sequential production of a variety of products simply by adjustment of the reactant feed rates and ratios.

Figure 2:
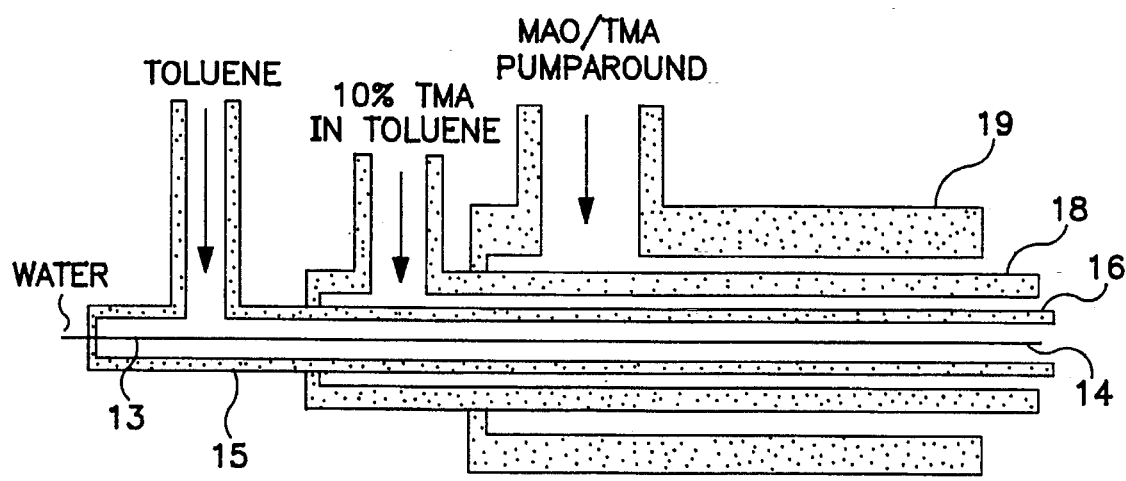
FIG. 2 is a schematic diagram showing a water injection system used in carrying out the embodiment of the process of the invention described in Example 1.

FIG. 2 illustrates a device which is suitable for introducing water to a solvent solution of aluminum alkyl in accordance with the process of the invention illustrated in FIG. 1. Water passes through a capillary tube 13 which is coaxially arranged within tube 15. The tip 14 of tube 13 is recessed about 1 to 2 mm from the end 16 of tube 15. Solvent passing through tube 15 sweeps water from tip 14 of tube 13 and carries the water into the TMA in solvent and pumparound mixture of TMA and MAO in solvent which enters through tubes 18 and 19 respectively and then into the mixing device (not shown). By using a flow of solvent to surround and sweep the water to the TMA containing mixture, plugging of the end of the water delivery tube due to aluminum oxide formation can be avoided.

Figure 4:
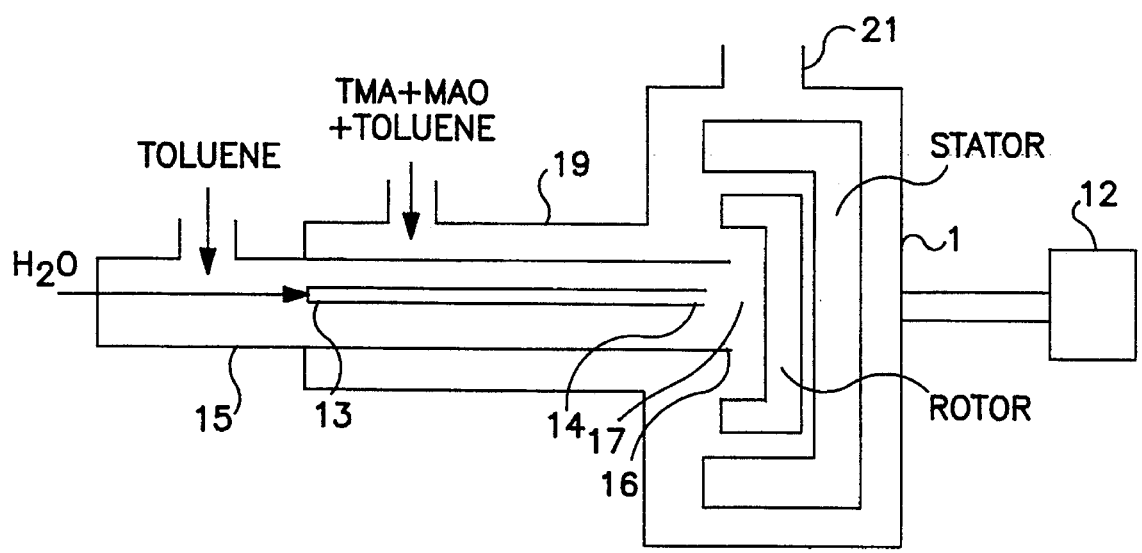
FIG. 4 is a schematic cross-sectional view of a water and solvent injector and in-line mixing system used in the embodiment of the process of the invention described in Examples 2 and 3.

FIG. 4 illustrates another device which is suitable for introducing water to a reaction zone in accordance with the process of the invention as illustrated in FIG. 3. The device is associated with reactor/stator in-line mixer 1 which is driven by motor 12. Water passes through a capillary tube 13 which is coaxially arranged within tube 15 which has a diameter of, for example, 3.0 mm. The tip 14 of capillary tube 13 is recessed about 1 to 2 mm from the end 16 of tube 15. Solvent passing through tube 15 sweeps water from tip 14 into the reaction zone 17 where the water reacts with a TMA-MAO-solvent mixture which enters reaction zone 17 through tube 19. The reaction mixture exits from rotor/stator in-line mixer 1 through outlet 21. The inner diameter of capillary tube 13 can be selected to deliver either a stream or individual droplets of water. For example, inner diameters of from 0.001 to 0.1 mm. The end of the water injection tube or nozzle should be positioned so that the water sprays out without contacting the walls of the solvent conduit. Otherwise, the water may collect on the walls because of the two immiscible liquid phases. In general, the ratio of the weight of the flow of solvent used to carry the water to the reaction zone to the weight of water ranges from about 10 to 1 to 1000 to 1 and preferably from about 25 to 1 to 150 to 1. Other suitable devices in which the end of a nozzle or tube carrying the water is positioned within a flow of solvent can be used to introduce water to the reaction. The water can be predispersed in a portion of the solvent. The shape of the tubes or conduits is not critical and they can have other than a circular cross-section. Also, other mixing devices can be used which provide high shear in the reaction zone including, but not limited to, ultrasonic, propeller and static mixers. In fact, it was found that a good product in high yield could be obtained even when the rotor/stator mixer was turned off. The hydrocarbylaluminum compounds and aluminoxane products are protected from oxygen and moisture by means of an inert gas atmosphere, such as dry nitrogen.

The volumes and flow rates of the water, solvent and recycle stream provide a very dilute concentration of water to give a more uniform hydrolysis reaction. For example, the total stream is at least 200 times the volume of water feed, preferably 5,000 times greater, and more preferably at least 8,000 times greater. The water is entirely soluble in the higher flow of solvent and plugging of the reactor, which can occur when using a continuous T-type reactor due to localized over reaction, is avoided. The result is a stable reaction without need of interruption to clear blockages. The high pumparound flow minimizes any temperature rise due to the highly exothermic hydrolysis reaction. Relative concentrations of water and hydrocarbylaluminum compound in the reaction zone can be maintained substantially constant by continually adding makeup hydrocarbyl aluminum and water in the proportions that they are reacted and removed from the pumparound flow.

The reaction feed and product removal rates are adjusted to give a concentration of crude aluminoxane product in solvent of from about 1 to 5 weight percent. The concentration of unreacted hydrocarbylaluminum can range from 0 to 10 weight percent. When making MAO, the MAO product concentration generally ranges from about 20 to 30 weight percent and unreacted TMA from about 2 to 10 weight percent based on the total weight of MAO, TMA and solvent. Feed rates depend upon the size of the reactor used. The crude aluminoxane product can be concentrated by the removal of solvent and unreacted alkylaluminum compound.

The process of the invention is further illustrated by, but is not intended to be limited to, the following examples.

EXAMPLE 1

Example 1 was run using a reactor and water injection system similar to that illustrated in FIGS. 1 and 2 to produce MAO. The flow rates were 2.80 kg/hour toluene, 0.04 kg/hour water, 2.26 kg/hour of 10 weight percent TMA in toluene and 13.18 kg/hour of the pumparound mixture of 96.1 weight percent toluene 1.6 weight percent TMA and 2.3 weight percent MAO. The reaction temperature was about 6° C. The tube and channel dimensions are given in Table 1. The tip 14 of water tube 13 was recessed about 1 mm from the end 16 of solvent tube 15, whose end 16 in turn extended abut 3 mm beyond the outlet of MAO tube 18. The inline mixer 1 was a IKA Works UTL 25 with a dispersion chamber and "fine dispersing elements" operating at about 11,700 rpm. No pluggage of capillary tube 13 was observed during 100 minutes of run time.

EXAMPLE 2

Example 2 was run using a reactor and water injection system similar to that illustrated in FIGS. 3 and 4 to produce MAO. The TMA in toluene was injected into the pumparound flow between the cooler and the pump. The flow rates were 2.55 kg/hour toluene, 0.02 kg/hour water, 3.03 kg/hour 10 weight percent TMA in toluene, and 682 kg/hour of the pumparound mixture of 1.9 weight percent TMA, 1.9 weight percent MAO and 96.2 weight percent toluene. The reaction temperature was about 6° C. The tube and channel dimensions are given in Table 1. The tip 14 of water capillary tube 13 was recessed about 1 mm from the end 16 of solvent tube 15. The inline mixer 1 was the same as used in Example 1 but the rotor was not turned on (0 rpm). No pluggage of capillary tube 13 was observed during 2 hours of run time.

EXAMPLE 3

Example 3 was run using an apparatus and mixer similar to that used for Example 2 to produce MAO. The flow rates were 2.0 kg/hour toluene, 0.05 kg/hour water, 5.4–5.7 kg/hour 10 weight percent TMA in toluene, and 682 kg/hour of pumparound mixture of 5.6 weight percent TMA, 3.4 weight percent MAO and 91 weight percent toluene. The reaction temperature was about 11° C. The tube and channel dimensions are given in Table 1. The inline mixer was operated at 7,000 rpm. No pluggage of capillary tube 13 was observed during 6 hours of operation.

Comparison

When the injection system was changed such that the tip 14 of water capillary tube 13 extended slightly past the end 16 of solvent tube 15, tip 14 plugged with white aluminum oxide in less than 1 minute after starting the water injection.

TABLE 1

| Example | Tube Dimensions | | | |
|---|---|---|---|---|
| | 1 | 2 | 3 | 4 |
| Water Capillary 13 ID[1] | 0.05 | 0.05 | 0.05 | 0.05 |
| Water Capillary 13 OD[2] | 0.35 | 0.35 | 0.35 | 0.35 |
| Solvent Tube 15 ID | 1.4 | 1.4 | 1.4 | 1.4 |
| Solvent Tube 15 OD | 3.2 | 3.2 | 3.2 | 3.2 |
| TMA Tube 18 ID | 4.6 | 4.6 | N/A[3] | N/A |
| TMA Tube 18 OD | 6.4 | 6.4 | N/A | N/A |
| Pumparound Tube 19 ID | 9.4 | 9.4 | 9.4 | 9.4 |
| Pumparound Tube 19 OD | 12.7 | 12.7 | 12.7 | 12.7 |

[1]ID = inner diameter in mm for each tube in list
[2]OD = outer diameter in mm for each tube in list
[3]N/A = not applicable (tube 18 does not exist)

EXAMPLE 4

Figure 5:
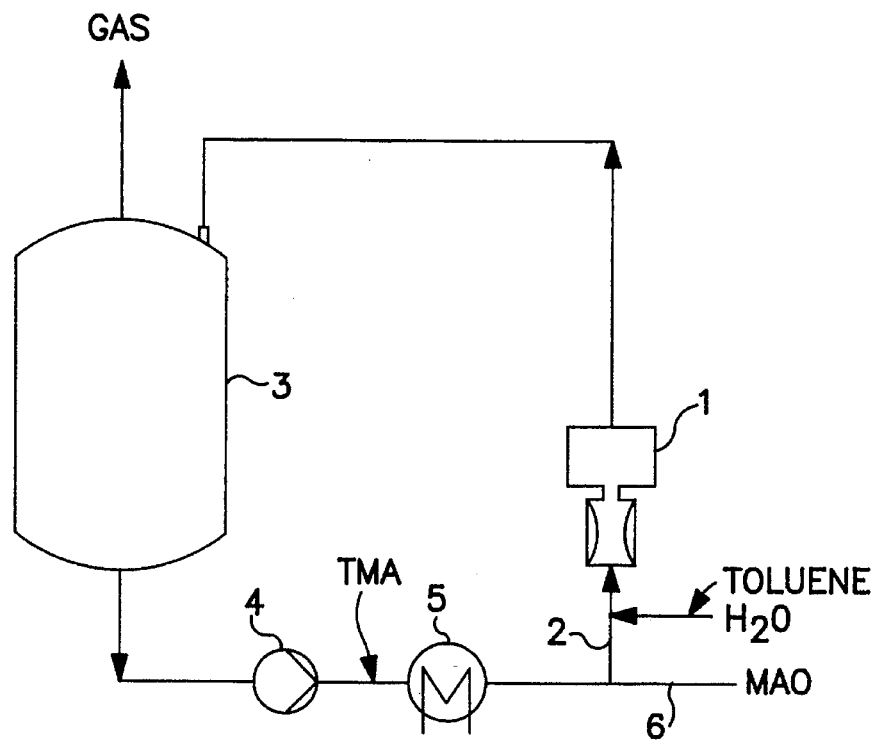
FIG. 5 is a schematic diagram showing a pumparound reactor system used in the embodiment of the process of the invention described in Example 4
Figure 6:
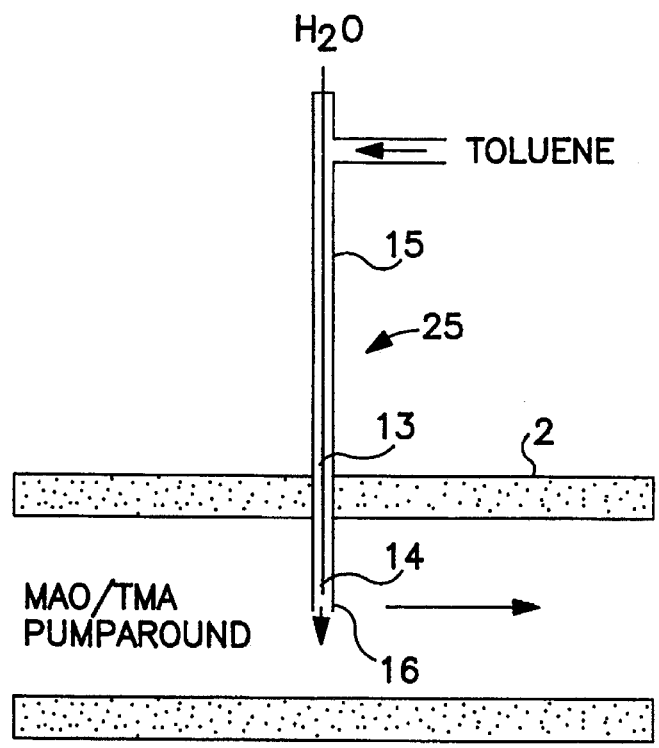
FIG. 6 is a schematic diagram showing a water injection system used in carrying out the embodiment of the process of the invention described in Examples 4 and 5.

The apparatus used is shown in FIGS. 5 and 6. The water was injected into the pumparound loop 2 ahead of mixer 1 rather than at the inlet. Injector system 25 as illustrated in FIG. 5 has the solvent tube 15 and water capillary tube 13 arranged about perpendicular to the flow of solvent, product MAO and unreacted TMA in pumparound loop 2. Tip 14 of tube 13 is recessed about 1 mm from the end 16 of tube 15. The inner diameter of water capillary tube 13 is 0.55 mm and its outer diameter is 0.65 mm. The inner diameter of solvent tube 15 is 1.4 mm and its outer diameter is 3.2 mm. The inner diameter of loop 2 is 9.4 mm and its outer diameter is 12.7 mm. The remainder of the system shown in FIG. 5 is the same as the system used in Example 2 (FIG. 3 ). The feeds were 12.3 weight percent TMA in toluene under nitrogen pressure, toluene (10 ppm water) under nitrogen pressure and deuterated water (purged with helium). The TMA solution and water were fed by metering pumps and the nitrogen was fed under nitrogen pressure. The degasser was charged with 3.65 kg (4.09 L) of TMA solution and the bulk temperature was brought down to 2°–3° C. The flow through the mixer was 522 kg/hr and the mixer was staged and set to run at 7500 rpm(t=0). The toluene feed was started at t=40 minutes (ave. 1.5 kg/hr, 16.3 gmol/hr); the TMA feed at t=48 minutes (ave. 6.0 kg/hr: 0.7 kg/hr TMA+5.26 kg/hr toluene, 10.2 gmol/hr TMA, 57.2 gmol/hr toluene); and the water feed at t=140 min (0.4 g min, 1.33 gmol/hr $H_2O$). The reaction zone temperature was 2°–3° C., the $H_2O$/TMA mole feed ratio was 0.13, the bulk/$H_2O$ flow volume ratio was about 24,000 and the bulk/$H_2O$ mass flow ratio was about 22,000. The expected Al weight percent was 3.7 weight percent and the residence time constant was 29 minutes. Crude MAO was continuously withdrawn to maintain a constant level in the system and collected at t=323 minutes, 6.3 time constants. After t=248 minutes, the mixer was turned off and two samples were analyzed to look at steady state. The results are shown in Table 2.

TABLE 2

| Sample | Time (+) Min | Time Constant | % Al | TMA Wt. % | % Vol Solids | Al as TMA |
|---|---|---|---|---|---|---|
| 1[(a)] | 248 | 3.7 | 3.53 | 7.95 | 0 | 84% |
| 2[(b)] | 423 | 9.8 | 3.68 | 8.28 | 0 | 84% |

[(a)]sampled just after the mixer was turned off
[(b)]mixer off

EXAMPLE 5

The apparatus used is shown in FIGS. 5 and 6 except that part of the pumparound flow was sent through a second cooler arranged in parallel with cooler 5 and reentered loop 2 after the crude MAO product removal point. This run was made without cleaning the water injection apparatus from Example 4. Total run time=11 hours. The rotor of mixer 1 was not turned on (rpm=0). The feed materials were the same as for Example 4 except that deionized water was used. The degasser was charged with 6.4 kg, 7.2 L of TMA solution (12.3%) and the bulk temperature was brought down to 1°–3° C. The flow through mixer 1 was 545 kg/hr. The TMA feed was started (t=0) (ave 8.2 kg/hr: 1.0 kg/hr TMA+7.2 kg/hr toluene, 14.0 gmol/hr TMA, 78 gmol/hr toluene) and then at t=6 minutes the toluene feed was started (ave. 1.2 kg/hr, 12.8 gmol/hr. The water feed was started at t=21 minutes (0.89 g/min, 3.0 gmol/hr $H_2O$). The reaction zone temperature was 1°–3° C., the $H_2O$ TMA molar feed ratio was 0.21, the bulk/$H_2O$ flow volume ratio was about 11,000 and the bulk/hr mass flow ratio was about 10,000. The expected Al weight percent was 3.99 weight percent and the residence time constant was 41 minutes. The crude MAO was continuously withdrawn to maintain a constant level and at t=213 minutes, 4.7 time constants collection was begun and ended at 273 minutes, 6.1 time constant with 10.9 kg collected. Analysis of a sample taken at t=270 minutes gave 3.73 wt percent Al, 7.5 weight percent TMA, 72% Al as TMA. No visible solids were immediately observed in the crude MAO samples. After about one week of storage at −15° C. a very faint film of solids appeared at the bottom of the sample bottles. Aluminum yield was estimated to be greater than 99%.

This invention is extraordinarily useful for adding water to aluminum alkyls without pluggage, so as to lower production costs through less downtime, less solvent recycle and better aluminum utilization. It provides a way to continuously add water to an aluminum alkyl and/or aluminoxane stream without process pluggage in immediate process piping. As long as the solvent is warm, it is also be possible to use this invention to inject water at subfreezing temperatures. The lower temperatures is expected to yield improvements in the reactor, particularly for the MAO pumparound production modes.

What is claimed is:

1. An improved process for making aluminoxane compositions by the addition of water to a solvent solution comprising a hydrocarbylaluminum compound and/or an aluminoxane in an organic solvent, the improvement comprising feeding said water through an orifice which is surrounded by a flow of solvent which carries said water into said solvent solution of hydrocarbylaluminum and/or aluminoxane.

2. The process of claim 1 wherein said water is fed through a first conduit which is surrounded by a second conduit which contains a flow of said solvent, the outlet of said first conduit being recessed from the outlet end of said second conduit.

3. The process of claim 2 wherein the outlet end of said first conduit is recessed at least about 1 mm from the outlet end of said second conduit.

4. The process of claim 1 wherein the ratio of the weight of said flow of solvent to the weight of water is from about 10 to 1 to 1000 to 1.

5. The process of claim 4 wherein the rate of the weight of said flow of solvent to the weight of water is from about 25 to 1 to 250 to 1.

6. The process of claim 1 wherein said hydrocarbylaluminum compound is trimethylaluminum and said aluminoxane composition is a methylaluminoxane.

* * * * *